United States Patent [19]
Muller

[11] Patent Number: 5,296,514
[45] Date of Patent: Mar. 22, 1994

[54] CORNEAL TREATMENT AGENTS

[75] Inventor: David F. Muller, Boston, Mass.

[73] Assignee: Summit Technology, Inc., Waltham, Mass.

[21] Appl. No.: 65,640

[22] Filed: May 21, 1993

Related U.S. Application Data

[63] Continuation-in-part of Ser. No. 855,308, Mar. 23, 1992, Pat. No. 5,214,071, which is a continuation-in-part of Ser. No. 690,081, Apr. 23, 1991, Pat. No. 5,098,896.

[51] Int. Cl.$^5$ ............................................. A62K 31/045
[52] U.S. Cl. ....................................... 514/724; 514/912
[58] Field of Search ................................ 514/724, 912

[56] References Cited

U.S. PATENT DOCUMENTS

| | | | |
|---|---|---|---|
| 3,584,115 | 6/1971 | Gebhart et al. | 424/45 |
| 4,738,956 | 4/1988 | Scott et al. | 514/179 |
| 4,874,794 | 10/1989 | Katz | 514/724 |
| 4,939,135 | 7/1990 | Robertson et al. | 514/179 |

FOREIGN PATENT DOCUMENTS

| | | |
|---|---|---|
| 127468 | 5/1984 | European Pat. Off. . |
| 2358662 | 6/1974 | Fed. Rep. of Germany . |
| 1393850 | 5/1975 | United Kingdom . |

OTHER PUBLICATIONS

Hood, C. I. et al. (1971) "The Corneal Reaction to Selected Chemical Agents in the Rabbit and Squirrel Monkey", *Am. J. Opthalmol.* 71(5):1009–1017.
Jordano, J. et al. (1974) "Bowen's Disease in Corneal Epithelium" *Arch. Soc. Esp. Oftal.* 34(8):723–730.
Johnson, W., Jr. (1988) "Final Report on the Safety Assessment of Cetearyl Alcohol, Cetyl Alcohol, Isostearyl Alcohol, Myristyl Alcohol and Behenyl Alcohol" *J. Am. Coll. Tox.* 7(3):359–413.

*Primary Examiner*—Zohreh A. Fay
*Attorney, Agent, or Firm*—Thomas J. Engellenner

[57] ABSTRACT

Aliphatic alcohols are disclosed for promoting corneal healing following injury to the eye. Such compositions ameliorate corneal discomfort, alleviate visual artifacts, and/or reduce irritation caused by the eye injury. The compositions also promote the regrowth of epithelial tissue over the corneal surface.

6 Claims, No Drawings

CORNEAL TREATMENT AGENTS

CROSS-REFERENCE TO RELATED APPLICATIONS

This application is a continuation-in-part of U.S. patent application Ser. No. 07/855,308, filed Mar. 23, 1992 now U.S. Pat. No. 5,214,071 which is a continuation of U.S. patent application Ser. No. 07/690,081, filed Apr. 23, 1991, now U.S. Pat. No. 5,098,896, issued Mar. 24, 1992.

BACKGROUND OF THE INVENTION

The technical field of this invention is corneal surgery and, in particular, the invention relates to methods and pharmaceutical compositions for treating the cornea following eye injuries resulting from surgical procedures on the eye, such as laser reprofiling operations. In addition, the method of this invention can be used to treat the cornea following eye injuries resulting from physical trauma to the eye or disease conditions of the eye.

Various surgical techniques are known for altering the surface of the cornea to correct refractive errors in vision. Such techniques include radial keratotomy ("RK") in which a set of radial incisions, i.e., resembling the spokes of a wheel, are made in the eye, down into the stroma of the cornea. As the incisions heal, the curvature of the eye is flattened, thereby remedying myopic conditions. Additionally, operations, such as keratoplasty, have been performed in which the surface of the cornea is sculpted to a new desired shape.

Until recently, such surgical operations on the cornea were most commonly carried out using diamond or steel knives or razors. However, corneal surgery, particularly with mechanical instruments, has often been less than satisfactory because the basement membrane upon which the epithelium attaches to the corneal proper is destroyed or damaged to an extent where epithelial cells cannot regrow and form a continuous protective layer over the surface of the eye.

Recently, new laser surgical techniques have been developed to ablate or otherwise treat corneal defects without mechanical abrasion. These techniques include photorefractive keratectomy ("PRK") and phototherapeutic keratectomy ("PTK") in which laser radiation is applied to the cornea with minimal heating effects to ablate or smooth refractive aberrations. Such laser techniques will usually create a pseudo basement membrane (or smooth anterior surface) on the outside of the cornea which facilitates epithelial cell attachment and, hence, healing of the eye.

Nonetheless, even with laser surgical approaches, there exists a need for methods and agents to facilitate corneal healing.

A new technique for corneal reshaping involves the use of a pulsed laser photoablation apparatus to ablate very thin layers of corneal tissue with greater precision than can typically be achieved with mechanical means. Such laser photoablation procedures typically employ a beam shaping or masking apparatus which varies the size of the exposure area on the corneal surface over time or provides a predefined profile of resistance to the laser radiation, such that areas of the cornea receive different cumulative exposures and thereby are ablated to varying depths.

These laser corneal reprofiling operations are typically referred to as photorefractive keratectomy ("PRK") and are performed with a high energy excimer laser which emits ultraviolet ("UV") laser radiation which is capable of ablating biological tissues without thermal damage to surrounding tissue. For further details on PRK techniques, see Marshall et al, "Photoablative Reprofiling Of The Cornea Using An Excimer Laser: Photorefractive Keratectomy," cit. Vol. I, *Lasers in Ophthalmology*, pp. 21–48 (1986) and U.S. Pat. Nos. 4,856,513 and 4,941,093.

In clinical trials of PRK procedures, patients typically experience some ocular discomfort immediately following surgery, together with a "cloudiness" in vision, which usually resolves itself in a matter of days or weeks.

There exists a need for methods for treating the newly reprofiled surface of the cornea to minimize the discomfort and visual artifacts that often accompany surgical procedures, such as PRK. This need is equally evident in cases wherein discomfort, visual artifacts, or irritation accompany eye injuries such as physical trauma to the eye or various disease conditions of the eye. In particular, compositions which can be topically applied to the eye in order to reduce discomfort and/or visual artifacts would satisfy an important medical need.

SUMMARY OF THE INVENTION

Aliphatic alcohols are disclosed for the promotion of corneal healing following injury to an eye and, in particular, for the promotion of corneal healing following eye injuries which result from surgical procedures on the cornea of the eye. Such compositions promote corneal healing following surgical procedures such as photorefractive keratectomies and corrective cataract surgery. In addition, these compositions can promote corneal healing following eye injury caused by physical trauma, such as damage through mechanical means or damage caused by chemicals that come in contact with the eye, or disease conditions. The compositions are preferably formulated in a physiologically compatible carrier which is non-irritating to the corneal surface and substantially inactive physiologically.

Eye injury refers to a condition of an eye other than its normal, healthy condition. For example, an eye injury can be any type of ulceration of the eye caused by a surgical procedure, physical trauma to the eye, or a disease condition. The eye injury can result in discomfort, visual artifacts, irritation, or destruction of the epithelial layer of the cornea. Corneal healing refers to improvement in the medical condition of the cornea. For example, corneal healing includes amelioration of discomfort (i.e. analgesia) and/or alleviation of visual artifacts (e.g. cloudiness) caused by the eye injury, reduction of irritation associated with the eye injury, and/or promotion of regrowth of damaged tissue, generally damaged epithelial tissue, over or around the cornea.

The aliphatic alcohols useful in the present invention preferably have chain lengths ranging from about C-20 to about C-26.

Particular aliphatic alcohols useful in the present invention include docosanol, tetracosanol and hexacosanol. The methods of the present invention can be practiced using the aliphatic alcohol compositions alone or together with other physiologically active agents, such as steroids, analgesics, growth factors, anti-oxidants, immunomodulators and/or antiallergenics.

Pharmaceutical carriers useful in the present invention include water and non-irritating organic compounds. When water is used to form an aqueous carrier, it is preferable to include dispersants or co-solvents to stabilize the formulation. Alternatively, ointments can be prepared, for example, using white petrolatum, water, and fatty acid esters and/or glycols to form a stable carrier. The active alcohols of the present invention can be added to the carrier in amounts ranging from about 0.2 to about 30% by weight, typically in the range of from about 1% to about 5% by weight.

It is preferable to employ aliphatic alcohols having a chain length ranging from about C-20 to about C-26. Shorter chain aliphatic articles tend to be irritants while longer chain aliphatic articles appear to have less efficacy in eye healing.

As known by those skilled in the art, the administration, sequence of administration and the concentration of the treatment agent depends upon a number of factors, including, the nature of the eye injury, the extent of the eye injury, the medical history, symptoms prior to, during or after the eye injury, and the extent of visual artifacts. Selection of a particular concentration or combination of aliphatic alcohols can be made by the skilled clinician guided by the foregoing description.

Methods of treatment during ophthalmic surgery with the compositions of the present invention can include the application of the compositions before laser exposure, during the procedures, and/or following the reprofiling operation. The compositions, in cases of eye injury caused by physical trauma or disease conditions, are generally applied after the physical trauma occurs or after manifestation of and/or during the course of a disease condition.

What is claimed is:

1. A method of promoting corneal healing following injury to an eye comprising:
    applying topically to the cornea of an injured eye, an aliphatic alcohol having a chain length ranging from about C-20 to about C-26 and in an amount effective to promote corneal healing.

2. The method of claim 1 wherein the aliphatic alcohol is docosanol.

3. The method of claim 1 wherein the aliphatic alcohol is tetracosanol.

4. The method of claim 1 wherein the aliphatic alcohol is hexacosanol.

5. The method of claim 1 wherein the aliphatic alcohol is applied in a concentration ranging from about 0.2 to about 30% by weight in a physiologically compatible carrier to the cornea.

6. The method of claim 1 wherein the aliphatic alcohol is applied in a concentration ranging from about 1 to about 5% by weight in a physiologically compatible carrier to the cornea.

* * * * *